(12) United States Patent
Toyohara et al.

(10) Patent No.: US 9,295,276 B2
(45) Date of Patent: Mar. 29, 2016

(54) FLAVOR IMPROVING AGENT

(71) Applicant: TAKASAGO INTERNATIONAL CORPORATION, Tokyo (JP)

(72) Inventors: Yoshikazu Toyohara, Kanagawa (JP); Tadahiro Hiramoto, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 150 days.

(21) Appl. No.: 14/154,092

(22) Filed: Jan. 13, 2014

(65) Prior Publication Data

US 2014/0127370 A1    May 8, 2014

Related U.S. Application Data

(63) Continuation of application No. 13/061,909, filed as application No. PCT/JP2009/065188 on Aug. 31, 2009, now abandoned.

(30) Foreign Application Priority Data

Sep. 2, 2008    (JP) .................................. 2008-224353

(51) Int. Cl.
| | |
|---|---|
| C07H 13/08 | (2006.01) |
| C07C 69/90 | (2006.01) |
| A23L 1/221 | (2006.01) |
| A23L 1/22 | (2006.01) |
| A23L 1/222 | (2006.01) |
| A61K 8/97 | (2006.01) |
| A61Q 11/00 | (2006.01) |

(52) U.S. Cl.
CPC .............. *A23L 1/2215* (2013.01); *A23L 1/222* (2013.01); *A23L 1/22075* (2013.01); *A23L 1/22083* (2013.01); *A61K 8/97* (2013.01); *A61Q 11/00* (2013.01); *C07C 69/90* (2013.01); *C07H 13/08* (2013.01); *A23V 2002/00* (2013.01); *C07C 2101/16* (2013.01)

(58) Field of Classification Search
CPC .... C07C 69/73; C07C 69/732; C07C 69/618; A23V 2250/2132
See application file for complete search history.

(56) References Cited

U.S. PATENT DOCUMENTS

| | | | |
|---|---|---|---|
| 8,933,217 B2 * | 1/2015 | Rinsch ................. | A23K 1/1612 536/119 |
| 2005/0147728 A1 | 7/2005 | Shioya et al. | |
| 2006/0286238 A1 * | 12/2006 | Zehentbauer et al. | ........ 426/534 |

FOREIGN PATENT DOCUMENTS

| | | |
|---|---|---|
| EP | 1334665 A1 | 8/2003 |
| JP | 47-023562 A | 10/1972 |
| JP | 08-256725 A | 10/1996 |
| JP | 10-042824 A | 2/1998 |
| JP | 10-052239 A | 2/1998 |
| JP | 11-075708 A | 3/1999 |
| JP | 11-318379 A | 11/1999 |
| JP | 2002-058427 A | 2/2002 |
| JP | 2003-299459 A | 10/2003 |
| JP | 2004-292778 A | 10/2004 |
| JP | 2006-238829 A | 9/2006 |
| JP | 2007-097594 A | 4/2007 |
| JP | 2009-189356 A | 8/2009 |

OTHER PUBLICATIONS

Chaisakdanugull et al., "Pineapple Juice and Its Fractions in Enzymatic Browning Inhibition of Banana [Musa (AAA Group) Gros Michel]" Journal of Agrucultural Food Chemistry (2007) vol. 55 pp. 4252-4257.*

U.S. Office Action issed in U.S. Appl. No. 13/061,909 dated May 6, 2014.

* cited by examiner

*Primary Examiner* — Eric Olson
(74) *Attorney, Agent, or Firm* — McDermott Will & Emery LLP

(57) ABSTRACT

Disclosed is a flavor improving agent that is a fraction derived from fruit juice or squeeze. A fraction wherein the amount of substance ratio between polyphenols and saccharides, the latter after acid hydrolysis of the fraction, (polyphenol/saccharide) is 0.1-10, and even more preferably, wherein the amount of substance ratio of the polyphenol and the saccharide before acid hydrolysis of the fraction (polyphenol/saccharide) is 1-100, and is used as a flavor improving agent. Such fraction are obtained with a method such as by a fruit juice or squeeze being absorbed onto a synthetic resin adsorbent and the adsorbed components being eluted by a solvent, or by extracting fruit juice or squeeze with ethanol. The flavor improving agent has flavor improving effects such as suppressing sourness, bitterness and astringency of foods and beverages, reducing harsh taste, contributing to a juice-like feel and contributing to a richness. In addition to foods and beverages, the flavor improving agent can also be added to pharmaceutical products or oral care products and the like, as well as to flavor composition.

7 Claims, No Drawings

FLAVOR IMPROVING AGENT

RELATED APPLICATIONS

This application is a Continuation of U.S. patent application Ser. No. 13/061,909, filed Mar. 2, 2011, which is the U.S. National Phase under 35 U.S.C. §371 of International Application No. PCT/JP2009/065188, filed on Aug. 31, 2009, which in turn claims the benefit of Japanese Application No. 2008-2274353, filed on Sep. 2, 2008, the disclosures of which are incorporated by reference herein.

TECHNICAL FIELD

The present invention relates to a flavor improving agent containing a fraction derived from fruit juice, which gives a juice-like feel or removes or reduces unpleasant tastes which foods and beverages have.

BACKGROUND ART

When eating foods or taking beverages, we feel various tastes among which are included tastes felt as unfavorable tastes. Bitterness, astringency, harsh taste, and the like are generally received as unfavorable tastes in many cases. Sourness is in some cases received as a favorable taste, but sourness with tongue-biting stimulus is received as an odd taste and is not acceptable for us. An attempt to suppress or reduce these unfavorable tastes has conventionally been made. Further, to the contrary, an attempt to enhance a juice-like feel or a volume feeling of foods and beverages, which are considered as favorable tastes, has been made as well.

As a method for improving the flavor of such foods and beverages, various methods such as methods of using fruits, fruit juices, squeezes or ingredients of fruits or fruit juices have also been known. As some of these methods, there are illustrated, for example, a method of reducing sourness or bitterness of foods by using a cranberry juice concentrate which has been subjected to decolorizing treatment and electrodialyzing treatment (see Patent Document 1), a method of giving a more natural body, a richness, and a thickness to foods and beverages by using vicenin-2 as an active ingredient (see Patent Document 2), a method of improving flavor of protein foods by adding an extract of grape seeds or grape skins (see Patent Document 3), a method of reducing various unfavorable smells and tastes of foods and beverages and improving flavor thereof by adding a hesperidin glycoside or a mixture of hesperidin glycoside and hesperidin (see Patent Document 4), a method of masking an astringent taste or a saltiness by compounding a berry in an oral composition containing hydroxycitric acid (see Patent Document 5), and a method of enhancing a richness, juiciness, body, and mildness to a taste of foods and beverages or of a composition for oral cavity by adding a high-boiling point fraction obtained in a dewaxing treatment of a citrus cold press oil (see Patent Document 6).

However, with the method of using a cranberry fruit juice concentrate described above, the process for preparing the raw material is so complicated that the method involves a problem in view of production cost. Also, with the method of using vicenin-2 as an active ingredient, an extent of the flavor-improving effect is limited, and a wider extent of the flavor-improving effect is demanded. Further, with the method of using an extract of grape seeds or grape skins, its application is limited to improvement of flavor of protein foods, thus the method involving a problem that its application is limited. The method of using a hesperidin glycoside or a mixture of hesperidin glycoside and hesperidin involves a problem that its flavor-improving effect is insufficient. The method of compounding a berry described above involves a problem that kinds of flavor to be improved are limited. The method of using a high-boiling point fraction obtained in a dewaxing treatment of a citrus cold press oil involves a problem that, since the flavor improving agent is an oil-soluble material, its application is limited.

As mentioned above, various methods for improving flavor of foods by using fruits, fruit juices, fruit juice ingredients, and the like have been conventionally known. However, these methods involve such problem as that foods to be used are limited, that the production process is complicated, or that the flavor-improving effect is insufficient. A flavor improving agent, therefore, is demanded which can exhibit its effects even when added to foods in only a small amount, which gives almost no taste or smell, which has a high safety, which can be produced at a low cost, and which can be widely used with respect to kinds of foods and beverages to be applicable and kinds of flavors to be improved. Such improvement of flavor is not limited only to foods and beverages but is required with pharmaceutical products to be used as oral compositions, oral care products, and the like as well. Also, by incorporating a flavor improving agent in a flavor composition which is used for these various products, flavor-improving effects can be given to the various products together with favorable aroma.

Additionally, it has been conventionally known to remove unpleasant smells liable to generate during storage of fruit juices by using a nonionic porous polymer resin (see Patent Document 7). However, it have not been confirmed that fruit juice components adsorbed on the resin have flavor-improving effects. It has also been known to produce a natural flavor by adsorbing aroma ingredients of fruit juice on a porous polymer resin and recovering it (see Patent Document 8). However, since its object is to recover an aroma, it is impossible to conduct removal of a solvent by distillation or conduct a heating, which cause lost of low-boiling point ingredients and thermal change of aroma.

PRECEDING TECHNICAL DOCUMENTS

Patent Documents

[Patent Document 1] JP-A 10-42824
[Patent Document 2] JP-A 2006-238829
[Patent Document 3] JP-A 11-75708
[Patent Document 4] JP-A 11-318379
[Patent Document 5] JP-A 10-52239
[Patent Document 6] JP-A 2003-299459
[Patent document 7] JP-A 47-23562
[Patent Document 8] JP-B 48-34234

SUMMARY OF THE INVENTION

Problems to be Solve by the Invention

The present invention has been made in view of the current circumstances above. An object of the invention, therefore, is to provide a flavor improving agent which can solve the conventional problems described above and, more specifically, to provide a flavor improving agent which can be produced by a simple method at a low production cost, which can exhibit a high flavor-improving effect even when added in only a small amount, which can give almost no taste or smell, which has a high safety, and which is applicable to a wide extent of products and has a wide extent of flavor-improving effects.

Further, another object of the invention is to provide a flavor composition, foods and beverages, pharmaceutical products and oral care products, whose flavors are improved.

Means for Solving the Problems

After intensive studies to solve the aforementioned problems, the present inventors have found that a specific fraction derived from fruit juice or squeeze, for example, a specific fraction obtained by bringing fruit juice or squeeze into contact with a synthetic resin adsorbent and then eluting the ingredient adsorbed on the synthetic resin adsorbent with a solvent, shows excellent effects as a flavor improving agent and the invention have been completed based on this finding.

That is, the invention relates to the following flavor improving agent, and a flavor composition, foods and beverages, pharmaceutical products, and oral care products containing the flavor improving agent.

[1] A flavor improving agent comprising a fraction derived from fruit juice or squeeze, wherein the amount of substance ratio between polyphenols and saccharides, the latter after acid hydrolysis of the fraction, (polyphenol/saccharide) is 0.1 to 10.
[2] The flavor improving agent described above, wherein the amount of substance ratio between polyphenols and saccharides before acid hydrolysis of the fraction, (polyphenol/saccharide) is 1 to 100.
[3] The flavor improving agent described in [1] or [2] above, wherein the fraction is obtained by adsorbing fruit juice or squeeze onto a synthetic resin adsorbent and then eluting the adsorbed ingredients with a solvent.
[4] The flavor improving agent described in any one of [1] to [3], wherein the fraction is an ethanol extract of fruit juice or squeeze.
[5] The flavor improving agent described in any one of [1] to [4], wherein the fruit is at least one member selected from among orange, lemon, grapefruit, lime, blueberry, strawberry, apple, pear, grape, melon, pineapple, peach, mango, and banana.
[6] The flavor improving agent described in any one of [1] to [5], wherein the flavor improving effect is at least one of suppressing sourness, bitterness or astringency, reducing harsh taste of vegetables, giving juice-like feel, and giving a richness.
[7] A flavor composition containing a flavor improving agent described in any one of [1] to [6] above.
[8] Foods and beverages containing a flavor improving agent described in any one of [1] to [6] above.
[9] A pharmaceutical product containing a flavor improving agent described in any one of [1] to [6] above.
[10] An oral care product containing a flavor improving agent described in any one of [1] to [6] above.

Advantageous Effects of the Invention

The flavor improving agent of the present invention can be produced by a simple procedure of adsorbing fruit juice or squeeze onto a synthetic resin adsorbent and then desorbing ingredients adsorbed on the synthetic resin adsorbent with a solvent, or of extracting fruit juice or squeeze with ethanol. In addition, as the starting material is fruit juice or squeeze, the flavor improving agent of the present invention is excellent in safety. The resulting flavor improving agent, therefore, can be used for a wide extent of products such as flavor compositions, foods and beverages, pharmaceutical products, oral care products, and the like to suppress their unfavorable tastes such as astringency, bitterness, and harsh taste. Further, the flavor improving agent can enhance favorable tastes such as improvement of a composite flavor of taste and smell, giving fruit-like feel and giving a richness. Thus, the flavor improving agent can be applied wider products and improve various kinds of flavor.

MODE FOR CARRYING OUT THE INVENTION

The flavor improving agent of the present invention and the process for obtaining it will be described hereinafter.

As a raw material for the flavor improving agent of the invention, fruit juice or squeeze is used. Fruits to be used as raw materials in the invention are not particularly limited and any one that is known as fruit can be used. To illustrate some of them, there are illustrated, for example, citrus fruits (e.g., orange, lemon, grapefruit, satsuma mandarin, *Citrus maxima, Citrus natsudaidai, Citrus hassaku*, lime, *Citrus medica, Citrus junos*, sweetie, *Citrus sudachi, Citrus sphaerocarpa*, Fortunella, etc.), berries (e.g., raspberries such as raspberry, blackberry, loganberry, youngberry, boysenberry, tayberry, cloudberry, salmonberry, arctic raspberry, mayberry, etc.; cowberries such as blueberry, cranberry, cowberry, etc.; currants such as gooseberry, red-currant, black-currant, etc.; silverberry; mulberry; strawberry; wolfberry; elderberry; etc.), pears (e.g., pear, Japanese pear, Chinese pear, etc.), apple, grape, pineapple, fig, melon, mango, pomegranate, passion fruit, litchi, banana, peach, watermelon, tomato, papaya, guava, Japanese medlar, and the like. As these fruit juices or squeeze, those which are commercially available may be used itself or may be directly obtained from fruits by, for example, incorporating a fruit juice- or squeeze-obtaining step as one step in a production process of obtaining the flavor improving agent. Further, since commercially available fruit juices or squeezes often contain solid materials such as fruit fibers, a treatment for removing the solid materials may be conducted using, for example, a filtering apparatus used in the production of foods, such as a press filter, a vacuum filter, a basket centrifugal filter or a separation plate type centrifugal filter. Additionally, in such treatment, a filtration aid or the like may be used as needed. These fruit juices or squeezes may be used alone or as a mixture of two or more thereof.

In the invention, a specific fraction obtained by subjecting the aforementioned fruit juice or squeeze to an appropriate treatment, i.e., a fraction wherein the amount of substance ratio between polyphenols and saccharides, the latter after acid hydrolysis of the fraction, (polyphenol/saccharide) is 0.1 to 10 is used as a flavor improving agent. The fraction is preferably a fraction wherein the amount of substance ratio between polyphenols and saccharides before acid hydrolysis of the fraction, (polyphenol/saccharide) is 1 to 100. Such fraction can be obtained by, for example, the following processes. However, the process for obtaining the specific fraction of the invention derived from fruit juice or squeeze is not limited only to these processes.

As a preferred process for obtaining the flavor improving agent of the invention, there is illustrated firstly a process of adsorbing fruit juice or squeeze onto a synthetic resin adsorbent and then desorbing the adsorbed ingredients with a solvent. As this process, a process of allowing fruit juice or squeeze to pass through the column in which synthetic resin adsorbent particles are filled as a fixing carrier to adsorb the fruit juice ingredients or squeeze ingredients onto the particles and then eluting the adsorbed fraction with a solvent to release the ingredients is preferably employed.

This process will be explained more specifically below. First, fruit juice or squeeze as it is or that after adjusting to an arbitrary concentration with water is allowed to pass through the column filled with the synthetic resin adsorbent particles. As the synthetic resin adsorbent used, there can be exemplified adsorbents composed of aromatic resins, acrylic resins, acrylonitrile series resins or the like. Such synthetic resin adsorbents are commercially available and there are illustrated, for example, DIAION HP20 and HP21, and SEPABEADS SP70 (these being aromatic resins and manufactured by Mitsubishi Chemical) ("DIAION" and "SEPABEADS" being registered trademarks; hereinafter the same), SEPABEADS SP825, SP850 and SP700 (these being aromatic high surface area resins and manufactured by Mitsubishi Chemical), SEPABEADS SP207 (aromatic modification resin; manufactured by Mitsubishi Chemical), DIAION HP20SS and SEPABEADS SP20SS and SP207SS (these being aromatic small-particle resins and being manufactured by Mitsubishi Chemical), AMBERLITE XAD2, XAD4, FPX66, XAD1180, XAD1180N, and XAD 2000 (these being styrene series resins and being manufactured by Organo Corporation) ("AMBERLITE" being a registered trademark; hereinafter the same), DIAION HP2MG (acrylic resin; manufactured by Mitsubishi Chemical), AMBERLITE XAD7HP (acrylic resin; manufactured by Organo Corporation), Sephadex LH20 (cross-linked dextran derivative; manufactured by GE Healthcare Bioscience) ("Sephadex" being a registered trademark), and the like. As the synthetic resin adsorbent, an appropriate one may be selected according to a kind or concentration of the fruit juice or squeeze to be use, which is to be allowed to pass through the column, or according to coexisting substances therein.

The amount of the synthetic resin adsorbent varies depending upon size of the column, an amount of fruit juice or squeeze to be allowed to pass, concentration of fruit juice or squeeze, a kind of solvent to be used, a kind of adsorbent to be used, and the like. An amount which provides optimal results, therefore, may be employed in consideration of these conditions, thus a preferred range thereof in a general sense not being determined. Usually, it suffices to use a 0.1- to 100-fold amount (by mass) of a synthetic resin adsorbent based on the soluble solid ingredients in fruit juice or squeeze to be allowed to pass since preferred results can usually be obtained when allowed to pass fruit juice or squeeze containing a 0.01- to 10-fold amount (by mass) of soluble solid components based on the synthetic resin adsorbent. However, preferred ranges of the amount of fruit juice or squeeze to be allowed to pass and of the amount of synthetic resin adsorbent to be used are not limited only to the above-described ranges. Further, the concentration of fruit juice or squeeze to be allowed to pass is not particularly limited but, when the concentration of fruit juice or squeeze is high, the pass-through speed cannot be increased so much due to the high viscosity thereof, a preferred fruit juice concentration is Bx. 50 or less, more preferably Bx. 20 or less.

Ingredients having the flavor improving effect in the fruit juice or squeeze are adsorbed to the absorbent by allowing the fruit juice or squeeze to pass through the aforementioned column. The pass-through amount and the pass-through speed of the fruit juice or squeeze vary depending upon size of the column, a kind of the synthetic resin adsorbent to be used, a kind of fruit juice or squeeze to be allowed to pass, and concentration of fruit juice or squeeze to be allowed to pass but, usually, SV=20 or less is preferred. After allowing fruit juice or squeeze to pass through the column, it is preferred to allow water to pass through the column to wash for removing fruit juice or squeeze and ingredients of the fruit juice or squeeze, which were not adsorbed to the resin but remaining in the column.

The ingredients adsorbed on the adsorbent resin are eluted and released by allowing a solvent to pass through the column. The eluting solvent is preferably selected from among water, ethanol, methanol, acetone, ethyl acetate, and a mixture thereof. Of these an ethanol-water mixed solvent is particularly preferred. In addition, it is more preferred to use a 50/50 to 99.5/0.5 (volume/volume) ethanol-water mixed solvent in order to elute ingredients having intended effects at room temperature efficiently. The components having the flavor-improving effect of the invention exist in a fraction eluted with the aforementioned solvent. The eluting speed varies depending upon size of the column, a kind of the solvent, a kind of the adsorbent resin, and the like. The eluting speed is not particularly limited, but is preferred to elute at an eluting speed of from 0.1 to 10 in SV and recover the fraction eluted within a 6-fold amount by volume of the resin. Additionally, SV (space velocity) is a unit for showing the volume per hour of liquid to be passed to volume of the resin.

A preferred but unlimited examples of a specific embodiment with respect to the adsorption treatment to and the desorption treatment from the synthetic resin for obtaining the flavor improving agent of the invention will be described below. That is, one of the examples comprise that fruit juice or squeeze is allowed to pass through a column filled with the aromatic resin or acrylic resin at a column temperature of 5 to 50° C. and then water is allowed to pass through the column for washing in the column, followed by eluting ingredients adsorbed on the resin in the column at a column temperature of 5° C. to 50° C. with a 50/50 to 99.5/0.5 (volume/volume) of ethanol-water mixed solvent to recover a fraction from the elution-initiating point to the point at which the amount of the eluted liquid reaches to a 6-fold volume amount or less of that of the resin. The eluate may be recovered by filtering by such a method as a press filtration, a suction filtration or a centrifugal filtration, as needed. Additionally, a filtration aid may be used upon the filtration. Further, since smell of the fraction itself is unnecessary in many cases in utilizing this fraction as a flavor improving agent for foods and beverages, the smell is removed by such a technique as concentration by heating or concentration under reduced pressure. Additionally, in the case where the smell of the fraction itself is not problematical, the removal of the smell may not be conducted.

Of the fractions obtained through such steps, those fractions wherein the amount of substance ratio between polyphenols and saccharides, the latter after acid hydrolysis of the fraction, (polyphenol/saccharide; PP/SG) is in the range of from 0.1 to 10, preferably in the range of from 0.2 to 3 are used as the flavor improving agents of the invention. Of such fractions, those fractions are preferred wherein the amount of substance ratio between polyphenols and saccharides before acid hydrolysis of the fraction (polyphenol/saccharide; hereinafter also referred to as PP/SG) is 1 to 100.

As other process, there is illustrated a process of directly extracting fruit juice or squeeze with a solvent such as alcohol, acetone or ethyl acetate. Of these, the extraction with ethanol is preferred. This process is preferably applied to concentrated fruit juice or concentrated squeeze. This process will be described specifically hereinafter. First, a high-concentration ethanol aqueous solution such as an ethanol aqueous solution of 95% or more is preferably used as the ethanol solution to be used for the ethanol extraction. This solution is mixed with concentrated fruit juice or concentrated squeeze and is sufficiently stirred. Then, it is allowed to stand, followed by recovering the supernatant. The supernatant is concentrated under reduced pressure to obtain a concentrate and again the high-concentration ethanol aqueous solution is added thereto, followed by sufficient stirring. The resulting solution is allowed to stand at a temperature of 10° C. or lower, preferably a sub-zero temperature, more preferably −10° C. or lower, followed by recovering the supernatant to obtain a specific fraction of the fruit juice or squeeze. Additionally, this process is illustrated for specifically describing the process of extracting fruit juice or squeeze with a solvent, and the process of extracting with a solvent is not limited only to this specifically illustrated process.

Further, the process for obtaining a specific fraction of the invention which is derived from fruit juice or squeeze is not limited only to the aforementioned two processes, but may be any other process. For example, a process of mixing two or more fractions not satisfying the condition of the invention with respect to PP/SG, and then adjusting the PP/SG value so as to satisfy the condition of the invention. Any process may be employed, but a fraction wherein a PP/SG value after hydrolysis is outside the range of from 0.1 to 10 fails to provide the effects of the invention described above even when used as a flavor improving agent.

The PP/SG value is obtained according to, for example, the following method. That is, a polyphenol amount in terms of chlorogenic acid is measured with Folin-Ciocalteu method and, separately, an amount of sugars (sucrose, fructose and glucose) is measured or an amount of sugars (sucrose, fructose, and glucose) after acid hydrolysis under the hydrolysis condition described below (1% addition of 35% hydrochloric acid, 100° C. and 7 hours) is measured according to the method for measuring an amount of sugars described below. The PP/SG value is calculated as molar ratio from the thus obtained amounts of the two substances.

Folin-Ciocalteu Method:

100 μL of a sample aqueous solution (the concentration being adjusted to about 2 mg/ml), 7.5 ml of water, and 300 μL of a 2-fold diluted aqueous solution of a phenol reagent (acidity: 1.8N) are added to a test tube and, after stirring, 1 ml of a 20% sodium carbonate aqueous solution and 1.1 ml of water are added thereto, followed by stirring. After the sample is allowed to stand for 1 hour at room temperature, the polyphenol amount of the sample in terms of chlorogenic acid is calculated from the absorbance at 765 nm based on a calibration curve which is prepared using chlorogenic acid.

Method of Measuring Sucroses:

A high-performance liquid chromatographic method (HPLC method) is employed.

Column: Shodex Asahipak $NH_2$ P-50 4E (4.6×250 mm; manufactured by Showa Denko K.K.)

Mobile phase: MeCN, $H_2O$

75→30% MeCN (0→60 min, Gradient), 30% MeCN (60-70 min, Isocratic)

Flow rate: 1 ml/min

Detector used: Evaporative light scattering detector (manufactured by Agilent)

Acid Hydrolysis Conditions:

A 5 mg/ml sample aqueous solution is prepared. After 50 μl of conc. (35%) hydrochloric acid is added to 5 ml of the prepared sample solution, the resulting mixture is refluxed in a 100° C. oil bath. After 7 hours are elapsed, the solution is cooled with ice and then 100 μl of aqueous ammonia (28%) is added thereto to discontinue the reaction. Thus, an acid-hydrolyzed sample is prepared.

The thus-obtained fraction derived from the fruit juice or squeeze with 0.1 to 10 in PP/SG after acid hydrolysis, more preferably the fraction whose PP/SG before acid hydrolysis is 1 to 100, can be used as it is as a flavor improving agent but, usually, after diluting it 2 to 500 times with distilled water, an ethanol aqueous solution or the like, the diluted fraction is used as a flavor improving agent.

The term "improvement of flavor" as used in the invention includes enhancement of favorable tastes such as giving a fruit-like feel and giving a richness as well as reduction of bitterness, astringency, sourness, and harsh taste and improvement of composite flavor of taste and smell with respect to various products including foods and beverages, pharmaceutical products, and oral care products.

As foods and beverages whose flavor can be improved with the flavor improving agent of the invention, there are illustrated foods and beverages such as health foods and beverages, foods and beverages containing fruit flavors, soups, and processed vegetable foods and beverages, but the foods and beverages of the invention are not limited only to these products. Of the above-described foods and beverages, health foods and beverages, foods and beverages containing fruit flavors, and processed vegetable foods and beverages are preferred.

The addition amount of the flavor improving agent of the invention and the method of adding the flavor improving agent can be properly selected according to kinds of foods and beverages to which the flavor improving agent is added. The addition amount is usually from 0.1 to 50,000 ppm, preferably 0.5 to 10,000 ppm for foods and beverages. The flavor improving agent of the invention can give sufficient flavor improving effects to foods and beverages when added in an amount within the above-described range. In case where the addition amount is less than the aforementioned range, the intended flavor improving effects might not be obtained in some cases. Also, in case where the addition amount is more than the aforementioned range, further improvement of the effects by the addition might not be obtained or inherent tastes of the foods and beverages might be spoiled in some cases.

As a method of adding the flavor improving agent of the invention, a method of mixing the flavor improving agent with foods and beverages whose flavor is required to be improved is usually employed. With processed foods, it is desirable to directly mix the flavor improving agent with a raw material whose flavor is required to be improved but, in the case where mixing with the raw material is difficult, it is possible to spray a solution of the flavor improving agent over the surface of the raw material whose flavor is required to be improved, or to dip the raw material in such solution, or to bring the raw material into contact with a powdery or sheet-like food containing the flavor improving agent.

Unlimited flavor improvements of foods and beverages with the flavor improving agent of the invention are illustrated below.

Improvement of Flavor of Health Foods and Beverages (Reduction of Bitterness, Astringency or Sourness)

Health foods and beverages include, for example, health foods and health beverages containing polyphenols, organic acids or other natural ingredients. In many cases, such health foods and beverages have unacceptable peculiar flavor. For example, foods and beverages containing polyphenols at a high concentration give bitterness and astringency. Foods and beverages containing an organic acid such as citric acid, lactic acid, acetic acid or ascorbic acid give a strong sourness. Bitterness, astringency, sourness and the like which these health foods and beverages have can be reduced by adding the flavor improving agent of the invention to such foods and beverages.

Improvement of Flavor of Foods and Beverages Containing Fruit Flavor (Giving a Fruit-Like Feel)

As the foods and beverages containing fruit flavor, there are illustrated fruit juice beverages, fruit juice-free beverages, carbonated beverages, sports beverages, lactic acid bacterium beverages, flavored tea, candy, gum, yogurt, gummy, jelly, chocolate, ice cream, and the like. Foods and beverages with a better taste to which a fruit-like feel is given can be provided by adding the flavor improving agent of the invention to such foods and beverages. Even when a flavor improving agent used was prepared from different fruit juice from the flavor of foods or beverages to which the flavor improving agent are added, a fruit-like feel can be given to the foods or beverages by adding the flavor improving agent of the invention.

Improvement of Flavor of Soups (Giving a Richness)

As soups, there are illustrated Western style soup, Japanese style soup, Chinese style soup, instant-noodle soup, ethnic soup, and the like. A richness can be given to the tastes of these soups by adding the flavor improving agent of the invention, thus more delicious soups being able to be provided.

Improvement of Flavor of Processed Vegetable Foods and Beverages (Reduction of Harsh Taste)

As processed vegetable foods and beverages, there can be illustrated beverages such as tomato juice, carrot juice, aojiru (green juice), and vegetable juice and processed foods such as jellies containing these. A harsh taste peculiar to vegetables can be reduced by adding the flavor improving agent of the invention to these processed vegetable foods and beverages.

The flavor improving agent of the invention may be mixed with various compounds or various known flavor raw materials to prepare flavor compositions. Since improvement of flavor is made on foods and beverages or other oral compositions, the flavor composition is particularly preferably a preparation flavor composition for foods and beverages.

Various compounds capable of being mixed with a flavor composition are not particularly limited as long as the effects of the flavor improving agent of the invention are not completely spoiled. As the compounds, there may be used additives commonly used for foods and beverages, pharmaceutical products and oral care products. Specifically, there can be illustrated sweeteners, acidulants, extenders, antioxidants, colorants, known antiseptics and antibacterial agents, emulsifiers, functional substances, existing flavor improving agents, pH-adjusting agents, milk components, nitrogen-containing compounds such as amino acids and peptides, and the like. These compounds may be compounded independently or in combination of two or more thereof. The compounding amount of the above-described compounds is not particularly limited as long as the objects of the invention can be attained.

Examples of the sweeteners described above include sugar, fructose, lactose, glucose, palatinose, maltose, trehalose, sorbitol, erythritol, maltitol, reduced palatinose, xylitol, lactitol, glutinous starch syrup, oligosaccharides, aspartame, sucralose, acesulfam K, saccharin, stevia, neotame, alitame, thaumatin, neohesperidin dihydrochalcone, licorice, and the like.

As the acidulants, there can be illustrated acetic acid, lactic acid, citric acid, and the like. As the extenders, there can be illustrated sugars, polysaccharides, processed starches, casein, gelatin, carboxymethyl cellulose, lecithin, and the like.

As the antioxidants, there are known pyrrolopyrrole derivatives, free radical scavengers obtained from extracts of various plants, enzymes having antioxidant properties such as superoxide dismutase and glutathione peroxidase, and the like as well as butylhydroxytoluene, butylhydroxyanisole, citric acid, bioflavo acid, glutathione, selenium, lycopene, vitamin A, vitamin E, vitamin C, etc., and these can be illustrated as the antioxidants.

As colorants, there are known natural colorants and organic synthetic colorants which are not hazardous to humans. Specific examples of the colorants include hibiscus colorant, huckleberry colorant, plum colorant, seaweed colorant, dewberry colorant, grape juice colorant, blackberry colorant, blueberry colorant, mulberry colorant, morello cherry colorant, redcurrant colorant, loganberry colorant, paprika powder, malt extract, rutin, flavonoids, red cabbage colorant, red radish colorant, adzuki bean colorant, turmeric colorant, olive tea, cowberry colorant, chlorella powder, saffron colorant, labiate colorant, strawberry colorant, chiocory colorant, pecan nut colorant, monascus colorant, safflower colorant, purple sweet potato colorant, lac colorant, spirlina colorant, onion colorant, tamarind colorant, red pepper colorant, Cape jasmine colorant, caramel colorant, lithospermum root colorant, rosewood colorant, krill colorant, orange colorant, carrot carotin, and the like.

As the known antiseptics and antibacterial agents, there can be illustrated benzoic acid, sodium benzoate, isopropyl p-hydroxybenzoate, isobutyl p-hydroxybenzoate, ethyl p-hydroxybenzoate, methyl p-hydroxybenzoate, butyl p-hydroxybenzoate, propyl p-hydroxybenzoate, sodium sulfite, sodium hyposulfite, potassium pyrosulfite, sorbic acid, potassium sorbate, sodium dehydroacetate, thujaplicin, udo extract, Japanese snowbell extract, *Artemisia capillaris* extract, oolong tea extract, soft roe protein extract, enzyme-decomposed *Coix lacryma-jobi* L. var. *ma-yuen* extract, tea catechins, apple polyphenols, pectin-decomposed substance, chitosan, lysozyme, $\epsilon$-polylysine, and the like.

As the emulsifiers, various emulsifiers having been conventionally used for foods and beverages can be used. Examples thereof include fatty acid monoglycerides, fatty acid diglycerides, fatty acid triglycerides, propylene glycol fatty acid esters, sugar fatty acid esters, polyglycerin fatty acid esters, lecithin, enzyme-processed lecithin, starch, processed starch, dextrin, sorbitan fatty acid esters, quillaja extract, gum arabic, tragacanth gum, guar gum, karaya gum, xanthan gum, pectin, alginic acid and salts thereof, carrageenan, gelatin, and casein.

The "functional substance" means a substance having a nutritious function or a living body adjusting function. As the functional substance, there are illustrated animal and plant fats and oils such as docosahexaenoic acid (DHA), eicosapentaenoic acid (EPA), DHA- and/or EPA-containing fish oil, linoleic acid, $\gamma$-linolenic acid, $\alpha$-linolenic acid, lecithin, diacylglycerol and the like, and derivatives thereof; animal and plant extracts such as rosemary, sage, perilla oil, chitin, chitosan, royal jelly, propolis and the like; vitamins, coenzymes and derivatives thereof such as vitamin A, vitamin D, vitamin E, vitamin F, vitamin K, coenzyme Q10, $\alpha$-lipoic acid and the like; polyphenols such as $\gamma$-oryzanol, catechin, anthocyanin, isoflavone, rutin, chlorogenic acid, theaflavin and the like; vegetable fibers such as hard-to-digest dextrin and the like; sugars such as palatinose, xylitol, oligosaccharide and the like; salts such as calcium citrate malate and the like; lactoprotein-derived substances such as casein phosphopeptide, lactoferrin, lactic peptide and the like; lactic bacteria; $\gamma$-aminobutyric acid; heme iron and the like.

The "pH-adjusting agent" means a substance or formulation usable for keeping the pH value of the food within an appropriate range. As the pH-adjusting agent, there are illustrated, for example, adipic acid, citric acid, trisodium citrate, glucono-$\delta$-lactone, gluconic acid, potassium gluconate, sodium gluconate, succinic acid, monosodium succinate, disodium succinate, sodium acetate, DL-tartaric acid, L-tartaric acid, DL-potassium hydrogen tartrate, L-potassium hydrogen tartrate, DL-sodium tartrate, L-sodium tartrate, potassium carbonate (anhydrous), sodium hydrogen carbonate, sodium carbonate, carbon dioxide, lactic acid, sodium lactate, glacial acetic acid, disodium dihydrogen pyrophosphate, fumaric acid, monosodium fumarate, DL-malic acid, DL-sodium malate, phosphoric acid, dipotassium hydrogen phosphate, potassium dihydrogen phosphate, disodium hydrogen phosphate, sodium dihydrogen phosphate, and other acidulants.

As the milk component, there are illustrated raw milk; milk; milk powder; skimmed milk powder; fresh cream, etc.; lactoprotein such as casein, whey and the like; substances derived from, for example, goat milk or sheep milk; and substances obtained by decomposing these materials or substances.

A known flavor improving agent such as sucralose, cyclodextrin, theanine, hesperidin glycoside, sugar cane extract or the like may be allowed to coexist with the flavor improving agent of the invention.

As the various flavor raw materials, there can be used, for example, natural aromas such as natural essential oils and various synthetic aromas. These aromas are not particularly limited as long as materials being able to use for foods and beverages, pharmaceutical products, and oral care products. As preferred aromas, there are illustrated, for example, synthetic aromas such as esters, alcohols, aldehydes, ketones, acetals, phenols, ethers, lactones, furans, hydrocarbons, and acids; natural aromas such as plant essential oils, e.g., essential oils of citrus fruits such as orange, lemon, lime, and grapefruit, essential oils prepared from flowers, peppermints, spearmints and spice oils, oily extracts such as kola nut extract, coffee extract, vanilla extract, cocoa extract, black tea extract, green tea extract, oolong tea extract and extracts of spices, and oleoresins, essences and recovered aromas thereof, etc.; and mixtures of plural aromas and essential oils selected from these materials. Further, there can also be used aromas described in, for example, "Investigation on the Actual Using State of Food Flavor Compounds in Japan" (Welfare Science Research Report, 2000; published in March 2001 by Japan Flavor and Fragrance Material Association), Gen-ichi Indo "Synthesized Flavor and Fragrances, Chemistry and Merchandise Information" (published on Mar. 6, 1996 by Chemical Daily Co., Ltd.), and Steffen Arctender "Perfume and Flavor Chemicals (Aroma Chemicals) 1, 2" (1969).

The compounding amount of the flavor improving agent is preferably from 0.001 to 50% based on the weight of the entire prepared flavor composition. The addition amount of the flavor composition to various products is preferably from 0.01 to 10%.

Further, the flavor improving agent of the invention can be added to a pharmaceutical product such as a liquid internal medicine to improve the taste of the medicine upon its uptake, thus providing a palatable pharmaceutical product. The compounding amount in this case may be in any range as long as the effect of improving the flavor can be obtained without inhibiting the medicinal effect of the pharmaceutical product. The amount thereof may be the same as the addition amount for ordinary foods and beverages.

Furthermore, the flavor improving agent of the invention may be added to oral care products. As the oral care products, there are illustrated, for example, toothpastes, mouth-cleaning products, mouthwashes, and the like. The addition amount in this case is also the same as the addition amount for foods and beverages.

EXAMPLES

The present invention will be described by reference to Examples. However, the invention is not limited only to such Examples. Additionally, in Examples, "%" means "% by weight" unless otherwise specified.

Example 1

Preparation of Flavor Improving Agent Derived from Pineapple Juice 800 g of water was added to 414 g of pineapple concentrated cloudy juice (Bx. 55; manufactured by Sanyo Foods Co., Ltd.) to dilute. The diluted fruit juice was mixed with 50 g of Celite 545 ("Celite" being a registered trademark; sold by Nacalai tesque), followed by suction filtration to obtain 1,055 g of a diluted fruit juice (Bx. 18.8) from which fibrous substances were removed. This juice was allowed to pass at a flow rate of SV=6 through a column (column size: inner diameter: 5 cm; height: 13.5 cm) filled with 180 g of AMBERLITE XAD-1180 (manufactured by Organo Corporation). After completion of the pass-through operation, 1,540 g of water was allowed to pass at SV=6 for washing. Next, 439 g of a 74% ethanol aqueous solution was allowed to pass at SV=2 to thereby elute adsorbed ingredients. 430 g of the thus-obtained eluate was mixed with 43 g of Celite 545 and, after suction filtration, the filtrate was diluted with ethanol and water to obtain 515 g of a sample of flavor improving agent derived from pineapple juice (solid content: 0.4%).

Polyphenol amounts in terms of chlorogenic acid in each 50 g of the raw fruit juice and the obtained sample were measured according to the aforementioned Folin-Ciocalteu method and, as a result, the polyphenol amount of the raw fruit juice was found to be 0.445 mmol, and that of the sample to be 0.174 mmol. Then, sugar amounts were measured according to the aforementioned predetermined method, and the sugar amount of the raw fruit juice was found to be 79.0 mmol, and that of the sample to be 0.0172 mmol. From these results, the raw fruit juice was found to have PP/SG before hydrolysis of 0.00563, and the sample was found to have PP/SG before hydrolysis of 10.1. Further, as a result of measuring the sugar amount in the same manner after acid hydrolysis according to the aforementioned predetermined method, the amount of sugar of the raw material was found to be 79.4 mmol and that of the sample was found to be 0.138 mmol. From these results, the raw fruit juice was found to have PP/SG after hydrolysis of 0.00560 and the sample was found to have PP/SG after hydrolysis of 1.26.

Comparative Example 1

Preparation of Comparative Sample Fraction a Derived from Pineapple Juice 800 g of water was added to 414 g of pineapple concentrated cloudy juice (Bx. 55; manufactured by Sanyo Foods Co., Ltd.) to dilute. The diluted fruit juice was mixed with 50 g of Celite 545, followed by suction filtration to obtain 1,055 g of a diluted fruit juice (Bx. 18.8) from which fibrous substances were removed. This juice was allowed to pass at a flow rate of SV=6 through a column (column size: inner diameter: 5 cm; height: 13.5 cm) filled with 180 g of AMBERLITE XAD-1180. After completion of the pass-through operation, 1,540 g of water was allowed to pass at SV=6 for washing. Subsequently, 439 g of a 74% ethanol aqueous solution was allowed to pass at SV=2 to recover an eluate. 430 g of the thus-obtained eluate was mixed with 43 g of Celite 545 and suction-filtered to obtain 410 g of a sample (solid content: 0.5%). After the solvent was removed by distillation using an evaporator, 15 g of ethyl acetate was added thereto to prepare a suspension. This suspension was loaded on a column (column size: inner diameter: 5 cm; height: 22 cm) filled with an ethyl acetate slurry of 200 g of silica gel BW-820MH (manufactured by Fuji Silysia Chemical Ltd.) for column chromatography, and eluted with 426 ml of ethyl acetate. Ethyl acetate was removed from the recovered eluate and the eluate was diluted with ethanol to obtain 100 g of a 50% ethanol solution.

The polyphenol amount in terms of chlorogenic acid in 50 g of the obtained sample was measured according to the aforementioned Folin-Ciocalteu method and, as a result, the polyphenol amount of the sample was found to be 0.0445 mmol. Then, sugar amounts were measured before and after acid hydrolysis according to the aforementioned predetermined method. The sugar amount of the sample before hydrolysis was found to be 0.00205 mmol and that of the sample after hydrolysis was found to be 0.00231 mmol. From these results, the sample was found to have PP/SG before hydrolysis of 21.7 and PP/SG after hydrolysis of 19.3.

Comparative Example 2

Preparation of Comparative Sample Fraction B Derived from Pineapple Juice 800 g of water was added to 414 g of pineapple concentrated cloudy juice (Bx. 55; manufactured by Sanyo Foods Co., Ltd.) to dilute. The diluted fruit juice was mixed with 50 g of Celite 545, followed by suction filtration to obtain 1,055 g of a diluted fruit juice (Bx. 18.8) from which fibrous substances were removed. This juice was allowed to pass at a flow rate of SV=6 through a column (column size: inner diameter: 5 cm; height: 13.5 cm) filled with 180 g of AMBERLITE XAD-1180 and the pass-through solution was recovered. Subsequently, 1,540 g of water was allowed to pass through the column at SV=6 to recover the pass-through solution. Further, 439 g of a 74% ethanol aqueous solution was allowed to pass through the column at SV=2 to recover an eluate. All of the recovered solutions were combined, mixed with 60 g of Celite 545, and suction-filtered to obtain 2,900 g of a resin-treated sample (solid content: 7.8%).

The polyphenol amount in terms of chlorogenic acid in 50 g of the obtained sample was measured according to the aforementioned Folin-Ciocalteu method and, as a result, the polyphenol amount of the sample was found to be 0.0619 mmol. Then, sugar amounts were measured before and after acid hydrolysis according to the aforementioned predetermined method. The sugar amount of the sample before hydrolysis was found to be 10.9 mmol and that of the sample after hydrolysis was found to be 10.9 mmol. From these results, the sample was found to have PP/SG before hydrolysis of 0.00567 and PP/SG after hydrolysis of 0.00567.

Examples 2 and 3, and Comparative Examples 3 to 6

Suppression of Sourness of Diluted Black Vinegar

Commercially available drinking vinegar "Jun Genmai Kurozu" (pure black vinegar of unpolished rice) (manufactured by Mizkan Co., Ltd.) was diluted with 4-fold amount of water, and the sample obtained in Example 1 which was derived from pineapple juice was added thereto to a concentration of 100 ppm to prepare a sample solution of Example 2 or added thereto to a concentration of 10,000 ppm to prepare a sample solution of Example 3. Also, for comparison, there were prepared a sample solution of Comparative Example 3 by adding the raw pineapple concentrated cloudy juice to Jun Genmai Kurozu to a concentration of 9,100 ppm, a sample solution of Comparative Example 4 by adding a 1% hesperidin mixture solution (hesperidin (manufactured by TCI):αG hesperidin (manufactured by Toyo Sugar Refining Co., Ltd.)=3:7) to Jun Genmai Kurozu to a concentration of 10,000 ppm, a sample solution of Comparative Example 5 by adding the comparative sample A obtained in Comparative Example 1 which was derived from pineapple juice to Jun Genmai Kurozu to a concentration of 1,950 ppm, and a sample solution of Comparative Example 6 by adding the comparative sample fraction B obtained in Comparative Example 2 which was derived from pineapple juice to Jun Genmai Kurozu to a concentration of 57,000 ppm. Additionally, the addition amounts of the comparative sample fractions A and B were determined as amounts corresponding to the addition amount of the sample solution of Example 3.

For examining difference between the sample solutions of Examples 2 and 3 and the comparative sample solutions by sensory evaluation, 6 panelists were asked to compare these by drinking. As a result, with the sample solution to which pineapple juice was added, 2 out of 6 panelists evaluated as "weak sourness-suppressing effect being recognized" and 4 panelists evaluated as "no effects being recognized". With the sample solution to which the hesperidin mixture solution was added, 3 out of 6 panelists evaluated as "weak sourness-suppressing effect being recognized" and 3 evaluated as "no effects being recognized". With the sample solution to which the comparative sample A derived from pineapple juice was added to a concentration of 1,950 ppm, 3 out of 6 panelists evaluated as "weak sourness-suppressing effect being recognized" and 3 evaluated as "no effects being recognized". With the sample solution to which the comparative sample fraction B was added, 2 out of 6 panelists evaluated as "weak sourness-suppressing effect being recognized" and 4 panelists evaluated as "no effects being recognized". In contrast, with the sample solution to which the sample of Example 1 derived from pineapple juice was added to a concentration of 100 ppm, 3 out of 6 panelists evaluated as "strong sourness-suppressing effect being recognized" and 3 panelists evaluated as "weak sourness-suppressing effect being recognized". Further, with the sample solution to which the sample of Example 1 derived from pineapple juice was added to a concentration of 10,000 ppm, 5 out of 6 panelists evaluated as "strong sourness-suppressing effect being recognized" and 1 panelist evaluated as "weak sourness-suppressing effect being recognized". Thus, no panelists evaluated the two sample solutions of Examples 2 and 3 as "no effects being recognized". Results of these are shown in Table 1.

TABLE 1

| | Flavor improving agent | Suppression effect of sourness | | |
|---|---|---|---|---|
| | | Strong | Weak | No effects |
| Example 2 | Fraction derived from pineapple juice: 100 ppm | 3 | 3 | 0 |
| Example 3 | Fraction derived from pineapple juice: 10,000 ppm | 5 | 1 | 0 |
| Comparative Example 3 | Pineapple juice | 0 | 2 | 4 |
| Comparative Example 4 | Hesperidin mixture | 0 | 3 | 3 |
| Comparative Example 5 | Comparative fraction A derived from pineapple juice | 0 | 3 | 3 |
| Comparative Example 6 | Comparative fraction B derived from pineapple juice | 0 | 2 | 4 |

From the above-described results, it has become apparent that the fraction of Example 1 derived from pineapple juice has the effect of reducing sourness of black vinegar. It is also seen that, even if the fraction is a fraction derived from pineapple juice, there is obtained only weak or almost no effect of improving the flavor in the case where the obtained fraction has PP/SG after acid hydrolysis outside the range of from 0.1 to 10.

Example 4 and Comparative Examples 7 and 8

Suppression of Sourness of Apple Vinegar

Commercially available drinking vinegar "Ringo Su" (apple vinegar) (manufactured by Mizkan Co., Ltd.) was diluted with 5.25-fold amount of water, and the sample obtained in Example 1 which was derived from pineapple juice was added thereto to a concentration of 10,000 ppm to prepare a sample solution of Example 4. Further, for comparison, there were prepared a sample solution of Comparative Example 7 by adding the raw pineapple concentrated cloudy juice to the diluted Ringo Su to a concentration of 9,100 ppm and a sample solution of Comparative Example 8 by adding a 1% hesperidin mixture solution (hesperidin (manufactured by TCI):αG hesperidin (manufactured by Toyo Sugar Refining Co., Ltd.)=3:7) to the diluted Ringo Su to a concentration of 10,000 ppm.

For examining difference between the sample solution of Example 4 and the comparative sample solutions by sensory evaluation, 11 panelists were asked to compare these by drinking. As a result, with the sample solution to which pineapple juice was added, 2 out of 11 panelists evaluated as "weak sourness-suppressing effect being recognized" and 9 panelists evaluated as "no effects being recognized". With the sample solution to which the hesperidin mixture solution was added, 5 out of 11 panelists evaluated as "weak sourness-suppressing effect being recognized", and 6 evaluated as "no effects being recognized". On the other hand, with the sample solution of Example 4, 8 out of 11 panelists evaluated as "strong sourness-suppressing effect being recognized", and 3 panelists evaluated as "weak sourness-suppressing effect being recognized", thus no panelists evaluating the sample solution of Example 4 as "no effects being recognized". Results are shown in Table 2.

TABLE 2

| | Flavor improving | Suppression effect of sourness | | |
| --- | --- | --- | --- | --- |
| | agent | Strong | Weak | No effects |
| Example 4 | Fraction derived from pineapple juice | 8 | 3 | 0 |
| Comparative Example 7 | Pineapple juice | 0 | 2 | 9 |
| Comparative Example 8 | Hesperidin mixture | 0 | 5 | 6 |

From the above-described results, it has become apparent that the fraction of Example 1 derived from pineapple juice has the effect of reducing sourness of apple vinegar.

Example 5 and Comparative Examples 9 and 10

Effect of Suppressing Bitterness and Astringency of Catechin

The sample obtained in Example 1 which was derived from pineapple juice was added to a commercially available drinking beverage "Healthya Water" (manufactured by Kao Corporation) rich in catechin (540 mg/500 ml) to a concentration of 1,000 ppm to prepare a sample solution of Example 5. Further, for comparison, there were prepared a sample solution of Comparative Example 9 by adding the raw pineapple concentrated cloudy juice to Healthya Water to a concentration of 910 ppm and a sample solution of Comparative Example by adding a 1% hesperidin mixture solution (hesperidin (manufactured by TCI):αG hesperidin (manufactured by Toyo Sugar Refining Co., Ltd.)=3:7) to Healthya Water to a concentration of 1,000 ppm.

For examining difference between the sample solution of Example 5 and the comparative sample solutions by sensory evaluation, 6 panelists were asked to compare these by drinking. As a result, with the sample solution to which pineapple juice was added, 2 out of 6 panelists evaluated as "weak bitterness- and astringency-suppressing effects being recognized" and 4 panelists evaluated as "no effects being recognized". With the sample solution to which the hesperidin mixture solution was added, 1 out of 6 panelists evaluated as "weak bitterness- and astringency-suppressing effects being recognized" and 5 evaluated as "no effects being recognized". On the other hand, with the sample solution of Example 5, 5 out of 6 panelists evaluated as "strong bitterness- and astringency-suppressing effects being recognized" and 1 panelist evaluated as "weak bitterness- and astringency-suppressing effects being recognized", thus no panelists evaluating the sample solution of Example 5 as "no effects being recognized". Results are shown in Table 3.

TABLE 3

| | Flavor improving | Suppression effect of bitterness and astringency | | |
| --- | --- | --- | --- | --- |
| | agent | Strong | Weak | No effects |
| Example 5 | Fraction derived from pineapple juice | 5 | 1 | 0 |
| Comparative Example 9 | Pineapple juice | 0 | 2 | 4 |
| Comparative Example 10 | Hesperidin mixture | 0 | 1 | 5 |

From the above-described results, it has become apparent that the fraction of Example 1 derived from pineapple juice has the effect of reducing bitterness and astringency of high-content catechin.

Example 6

Preparation of Flavor Improving Agent Derived from Grape Juice 216 g of 95 v/v % ethanol was added to 144 g of concentrated grape juice (Bx. 68; manufactured by TECNOVIN DO BRAZIL IND.) and after sufficiently mixing, the mixture was allowed to stand at room temperature for 2 hours. After the mixture was allowed to stand, the supernatant was recovered to obtain 240 g of a solution. This solution was concentrated under reduced pressure to obtain 60 g of a concentrated liquid. 60 g of 95 v/v % ethanol was added to this concentrated liquid and, after sufficiently stirring, the mixture was allowed to stand at −20° C. for 18 hours. After the mixture was allowed to stand, the supernatant was recovered and 75 g of the thus-obtained solution (solid content: 12.0%) was referred to as a sample of flavor improving agent derived from grape juice. This sample did not have grape-like aroma.

Polyphenol amounts in terms of chlorogenic acid in each 50 g of the raw fruit juice and the obtained sample were measured. As a result, the polyphenol amount of the raw fruit juice was found to be 3.22 mmol and that of the sample to be 3.82 mmol. Then, sugar amounts were measured according to the aforementioned predetermined method. The sugar amount of the raw fruit juice was found to be 137 mmol and that of the sample to be 3.12 mmol. From these results, the raw fruit juice was found to have PP/SG before hydrolysis of 0.0235 and the sample was found to have PP/SG before hydrolysis of 1.22. Also, as a result of measuring the sugar amount in the same manner after acid hydrolysis, the amount of sugar of the raw material was found to be 156 mmol and that of the sample was found to be 25.6 mmol. From these results, the raw fruit juice was found to have PP/SG after hydrolysis of 0.0206 and the sample was found to have PP/SG after hydrolysis of 0.149.

Example 7 and Comparative Examples 11 and 12

Effect of Suppressing Harsh Taste of Vegetables

The sample obtained in Example 6 which was derived from grape juice was added to commercially available green juice "Super Aojiru" (manufactured by Fancl Corporation) to a concentration of 10,000 ppm to prepare a sample solution of Example 7. Further, for comparison, there were prepared a sample solution of Comparative Example 11 by adding the raw grape concentrated juice to Super Aojiru to a concentration of 19,800 ppm and a sample solution of Comparative Example 12 by adding a 1% hesperidin mixture solution (hesperidin (manufactured by TCI):αG hesperidin (manufactured by Toyo Sugar Refining Co., Ltd.)=3:7) to Super Aojiru to a concentration of 25,000 ppm.

For examining difference between the sample solution of Example 7 and the comparative sample solutions by sensory evaluation, 8 panelists were asked to compare these by drinking. As a result, with the sample solution to which grape juice was added, 3 out of 8 panelists evaluated as "weak harsh taste-suppressing effect being recognized" and 5 panelists evaluated as "no effects being recognized". With the sample solution to which the hesperidin mixture solution was added, 3 out of 8 panelists evaluated as "weak harsh taste-suppressing effect being recognized" and 5 evaluated as "no effects being recognized". On the other hand, with the sample solution of Example 7, 6 out of 8 panelists evaluated as "strong harsh taste-suppressing effect being recognized" and 2 panelists evaluated as "weak harsh taste-suppressing effect being recognized", thus no panelists evaluating the sample solution of Example 7 as "no effects being recognized". Results are shown in Table 4.

TABLE 4

| | Flavor improving agent | Suppression effect of harsh taste | | |
|---|---|---|---|---|
| | | Strong | Weak | No effects |
| Example 7 | Fraction derived from grape juice | 6 | 2 | 0 |
| Comparative Example 11 | Grape juice | 0 | 3 | 5 |
| Comparative Example 12 | Hesperidin mixture | 0 | 3 | 5 |

From the above-described results, it has become apparent that the fraction of Example 6 derived from grape juice has the effect of reducing harsh taste of vegetables.

Example 8

Preparation of Flavor Improving Agent Derived from Peach Juice 257 g of water was added to 245 g of concentrated peach juice (Bx. 40.5; manufactured by Sanyo Foods Co., Ltd.) to dilute. The water-diluted peach juice obtained had Bx. 19.8. The diluted fruit juice was allowed to pass at a flow rate of SV=5 through a column (column size: inner diameter: 5 cm; height: 11 cm) filled with 150 g of AMBERLITE XAD-1180 (manufactured by Organo Corporation). After completion of the pass-through operation, 1,300 g of water was allowed to pass at SV=5 for washing. Next, 370 g of a 74% ethanol aqueous solution was allowed to pass at SV=2.5 to thereby elute adsorbed ingredients. 379 g of the thus-obtained eluate was mixed with 4 g of Celite 545 and, after suction filtration, there was obtained 366 g of a filtrate (solid content: 0.25%) which was referred to as a sample of flavor improving agent derived from peach juice.

Polyphenol amounts in terms of chlorogenic acid in each 50 g of the raw fruit juice and the obtained sample were measured and, as a result, the polyphenol amount of the raw fruit juice was found to be 0.145 mmol and that of the sample to be 0.0349 mmol. Then, sugar amounts were measured according to the aforementioned predetermined method. The sugar amount of the raw fruit juice was found to be 70.4 mmol and that of the sample to be 0.00914 mmol. From these results, the raw fruit juice was found to have PP/SG before hydrolysis of 0.0206 and the sample was found to have PP/SG before hydrolysis of 3.82. Also, as a result of measuring the sugar amount in the same manner after acid hydrolysis, the amount of sugar of the raw material was found to be 70.8 mmol and that of the sample was found to be 0.107 mmol. From these results, the raw fruit juice was found to have PP/SG after hydrolysis of 0.00205 and the sample was found to have PP/SG after hydrolysis of 0.326.

Example 9 and Comparative Example 13

Effect of Giving a Richness

A soup was prepared from commercially available powdered corn soup "Knorr Cup Soup Corn Cream" (manufactured by Ajinomoto Co., Inc.) ("Knorr" is a registered trade mark.) according to the instruction. The sample obtained in Example 8 which was derived from peach juice was added to the soup to a concentration of 40,000 ppm to prepare a sample solution of Example 9. Further, for comparison, a sample solution of Comparative Example 13 was prepared by adding the raw peach juice to the soup to a concentration of 25,000 ppm.

For examining difference between the sample solution of Example 9 and the comparative sample solutions by sensory evaluation, 10 panelists were asked to compare these by drinking. As a result, with the sample solution to which peach juice was added, 1 out of 10 panelists evaluated as "weak effect of giving a richness being recognized" and 9 panelists evaluated as "no effects being recognized". On the other hand, with the sample solution of Example 9, 7 out of 10 panelists evaluated as "strong effect of giving a richness being recognized" and 3 panelists evaluated as "weak effect of giving a richness being recognized", thus no panelists evaluating the sample solution of Example 9 as "no effects being recognized". Results are shown in Table 5.

TABLE 5

| | Flavor improving agent | Effect of giving a richness | | |
| --- | --- | --- | --- | --- |
| | | Strong | Weak | No effects |
| Example 9 | Fraction derived from peach juice | 7 | 3 | 0 |
| Comparative Example 13 | Peach juice | 0 | 1 | 9 |

From the above-described results, it has become apparent that the fraction of Example 8 derived from peach juice has the effect of giving a richness.

Example 10

Preparation of Flavor Improving Agent Derived from Apple Juice 311 g of water was added to 189 g of concentrated apple juice (Bx. 53; manufactured by Aomori Ringo Kako K.K.) to dilute. The water-diluted apple juice obtained had Bx. 20.2. The diluted fruit juice was allowed to pass at a flow rate of SV=5 through a column (column size: inner diameter: 5 cm; height: 5 cm) filled with 70 g of AMBERLITE XAD-2 (manufactured by Organo Corporation). After completion of the pass-through operation, 500 g of water was allowed to pass at SV=5 for washing. Next, 170 g of a 74% ethanol aqueous solution was allowed to pass through the column at SV=3 to thereby elute adsorbed ingredients. 175 g of the thus-obtained eluate was heated to 60° C. and concentrated under reduced pressure to obtain 0.33 g of a solid product. 33 g of a 74% ethanol aqueous solution was added thereto to dissolve the solid product, followed by suction filtration to obtain 28 g of a filtrate (solid content: 1.0%) which was referred to as a sample of flavor improving agent derived from apple juice. This sample did not have an apple-like aroma.

Polyphenol amounts in terms of chlorogenic acid in each 50 g of the raw fruit juice and the obtained sample were measured and, as a result, the polyphenol amount of the raw fruit juice was found to be 0.396 mmol and that of the sample to be 1.04 mmol. Then, sugar amounts were measured according to the aforementioned predetermined method, and the sugar amount of the raw fruit juice was found to be 119 mmol and that of the sample to be 0.0268 mmol. From these results, the raw fruit juice was found to have PP/SG before hydrolysis of 0.00333 and the sample was found to have PP/SG before hydrolysis of 38.8. Also, as a result of measuring the sugar amount in the same manner after acid hydrolysis, the amount of sugar of the raw material was found to be 119 mmol and that of the sample was found to be 0.429 mmol. From these results, the raw fruit juice was found to have PP/SG after hydrolysis of 0.00333 and the sample was found to have PP/SG after hydrolysis of 2.42.

Example 11 and Comparative Example 14

Effect of Giving a Juice-Like Feel

Water was added to 214 g of high fructose corn syrup and 2.6 g of citric acid to prepare 400 g of an aqueous solution and, further, 1600 g of carbonated water and 2 g of a grapefruit flavor were added thereto to prepare a material. The sample obtained in Example 10 which was derived from apple juice was added to this material to a concentration of 2,000 ppm to prepare a sample solution of Example 11. Also, for comparison, a sample solution of Comparative Example 14 was prepared by adding the raw apple juice to the material to a concentration of 1,400 ppm.

For examining difference between the sample solution of Example 11 and the comparative sample solution by sensory evaluation, 10 panelists were asked to compare these by drinking. As a result, with the sample solution to which apple juice was added, 4 out of 10 panelists evaluated as "weak effect of giving a juice-like feel being recognized" and 6 panelists evaluated as "no effects being recognized". On the other hand, with the sample solution of Example 11, 8 out of 10 panelists evaluated as "strong effect of giving a juice-like feel being recognized" and 2 panelists evaluated as "weak effect of giving a juice-like feel being recognized", thus no panelists evaluating the sample solution of Example 11 as "no effects being recognized". Results are shown in Table 6.

TABLE 6

| | Flavor improving agent | Suppression effect of harsh taste | | |
| --- | --- | --- | --- | --- |
| | | Strong | Weak | No effects |
| Example 11 | Fraction derived from apple juice | 8 | 2 | 0 |
| Comparative Example 14 | Apple juice | 0 | 4 | 6 |

From the above-described results, it has become apparent that the fraction of Example 10 derived from apple juice has the effect of giving a juice-like feel.

Example 12

Preparation of Flavor Improving Agent Derived from Strawberry Juice 155 g of water was added to 356 g of concentrated strawberry juice (Bx. 28.3; manufactured by IWATABUSSAN CO., LTD) to dilute. The water-diluted strawberry juice obtained had Bx. 19.8. The diluted fruit juice was allowed to pass at a flow rate of SV=8 through a column (column size: inner diameter: 5 cm; height: 7.5 cm) filled with 100 g of DIAION HP20 (manufactured by Mitsubishi Chemical). After completion of the pass-through operation, 890 g of water was allowed to pass through the column at SV=8 for washing. Next, 300 g of a 74% ethanol aqueous solution was allowed to pass through the column at SV=3 to thereby elute adsorbed ingredients. 290 g of the thus-obtained eluate was mixed with 3 g of Celite 545, followed by suction filtration to obtain 278 g of a filtrate (solid content: 0.29%) which was referred to as a sample of flavor improving agent derived from strawberry juice.

Polyphenol amounts in terms of chlorogenic acid in each 50 g of the raw fruit juice and the obtained sample were measured and, as a result, the polyphenol amount of the raw fruit juice was found to be 0.289 mmol and that of the sample to be 0.181 mmol. Then, sugar amounts were measured according to the aforementioned predetermined method. The sugar amount of the raw fruit juice was found to be 45.5 mmol and that of the sample to be 0.00863 mmol. From these results, the raw fruit juice was found to have PP/SG before hydrolysis of 0.00635 and the sample was found to have PP/SG before hydrolysis of 21.0. Also, as a result of measuring the sugar amount in the same manner after acid hydrolysis, the amount of sugar of the raw material was found to be 45.7 mmol and that of the sample was found to be 0.185 mmol. From these results, the raw fruit juice was found to have PP/SG after hydrolysis of 0.00632 and the sample was found to have PP/SG after hydrolysis of 0.978.

Example 13 and Comparative Example 15

Effect of Giving a Juice-Like Feel

Water was added to 214 g of high fructose corn syrup and 2.6 g of citric acid to prepare 400 g of an aqueous solution and, further, 1600 g of carbonated water and 2 g of an apple flavor were added thereto to prepare a material. The sample obtained in Example 12 which was derived from strawberry juice was added to the material to a concentration of 1,400 ppm to prepare a sample solution of Example 13. Also, for comparison, a sample solution of Comparative Example 15 was prepared by adding the raw strawberry juice to a concentration of 1,800 ppm.

For examining difference between the sample solution of Example 13 and the comparative sample solution by sensory evaluation, 10 panelists were asked to compare these by drinking. As a result, with the sample solution to which strawberry juice was added, 3 out of 10 panelists evaluated as "weak effect of giving a juice-like feel being recognized" and 7 panelists evaluated as "no effects being recognized". On the other hand, with the sample solution of Example 13, 6 out of 10 panelists evaluated as "strong effect of giving a juice-like feel being recognized" and 4 panelists evaluated as "weak effect of giving a juice-like feel being recognized", thus no panelists evaluating the sample solution of Example 13 as "no effects being recognized". Results are shown in Table 7.

TABLE 7

| | Flavor improving agent | Effect of giving a juice-like feel | | |
|---|---|---|---|---|
| | | Strong | Weak | No effects |
| Example 13 | Fraction derived from strawberry juice | 6 | 4 | 0 |
| Comparative Example 15 | Strawberry juice | 0 | 3 | 7 |

From the above-described results, it has become apparent that the fraction of Example 12 derived from strawberry juice has the effect of giving a juice-like feel.

Example 14

Preparation of Flavor Improving Agent Derived from Blueberry Juice 346 g of water was added to 155 g of concentrated blueberry juice (Bx. 65.1; manufactured by Eiko Boeki K.K.) to dilute. The water-diluted blueberry juice obtained had Bx. 20.8. The diluted fruit juice was allowed to pass at a flow rate of SV=5 through a column (column size: inner diameter: 10.5 cm; height: 8.5 cm) filled with 500 g of DIAION HP20 (manufactured by Mitsubishi Chemical). After completion of the pass-through operation, 4,500 g of water was allowed to pass through the column at SV=6 for washing. Next, 1,250 g of a 74% ethanol aqueous solution was allowed to pass through the column at SV=2 to thereby elute adsorbed ingredients. 1,300 g of the thus-obtained eluate was mixed with 15 g of Celite 545, followed by suction filtration to obtain 1,250 g of a filtrate (solid content: 0.25%) which was referred to as a sample of flavor improving agent derived from blueberry juice.

Polyphenol amounts in terms of chlorogenic acid in each 50 g of the raw fruit juice and the obtained sample were measured and, as a result, the polyphenol amount of the raw fruit juice was found to be 4.52 mmol and that of the sample to be 0.436 mmol. Then, sugar amounts were measured according to the aforementioned predetermined method. The sugar amount of the raw fruit juice was found to be 119 mmol and that of the sample to be 0.00846 mmol. From these results, the raw fruit juice was found to have PP/SG before hydrolysis of 0.0380 and the sample was found to have PP/SG before hydrolysis of 51.5. Also, as a result of measuring the sugar amount in the same manner after acid hydrolysis, the amount of sugar of the raw material was found to be 121 mmol and that of the sample was found to be 0.223 mmol. From these results, the raw fruit juice was found to have PP/SG after hydrolysis of 0.0374 and the sample was found to have PP/SG after hydrolysis of 1.96.

Example 15 and Comparative Example 16

Effect of Giving a Juice-Like Feel

Water was added to 214 g of high fructose corn syrup and 2.6 g of citric acid to prepare 400 g of an aqueous solution and, further, 1,600 g of carbonated water and 2 g of a peach flavor were added thereto to prepare a material. The sample obtained in Example 14 which was derived from blueberry juice was added to this material to a concentration of 1,600 ppm to prepare a sample solution of Example 15. Further, for comparison, a sample solution of Comparative Example 16 was prepared by adding the raw blueberry juice to a concentration of 230 ppm.

For examining difference between the sample solution of Example 15 and the comparative sample solution by sensory evaluation, 10 panelists were asked to compare these by drinking. As a result, with the sample solution to which blueberry juice was added, 2 out of 10 panelists evaluated as "weak effect of giving a juice-like feel being recognized" and 8 panelists evaluated as "no effects being recognized". On the other hand, with the sample solution of Example 15, 6 out of 10 panelists evaluated as "strong effect of giving a juice-like feel being recognized" and 4 panelists evaluated as "weak effect of giving a juice-like feel being recognized", thus no panelists evaluating the sample solution of Example 15 as "no effects being recognized". Results are shown in Table 8.

TABLE 8

| | Flavor improving agent | Effect of giving a juice-like feel | | |
|---|---|---|---|---|
| | | Strong | Weak | No effects |
| Example 15 | Fraction derived from blueberry juice | 6 | 4 | 0 |
| Comparative Example 16 | Blueberry juice | 0 | 2 | 8 |

From the above-described results, it has become apparent that the fraction of Example 14 derived from blueberry juice has the effect of giving a juice-like feel.

Example 16

Preparation of Flavor Improving Agent Derived from Mango Juice 350 g of water was added to 150 g of concentrated mango juice (Bx. 66.1; manufactured by Eiko Boeki K.K.) to dilute.

The water-diluted mango juice obtained had Bx. 20.3. The diluted fruit juice was allowed to pass at a flow rate of SV=4 through a column (column size: inner diameter: 5 cm; height: 9 cm) filled with 120 g of DIATOM HP20 (manufactured by Mitsubishi Chemical). After completion of the pass-through operation, 1,060 g of water was allowed to pass through the column at SV=6 for washing. Next, 300 g of a 74% ethanol aqueous solution was allowed to pass through the column at SV=1 to thereby elute adsorbed ingredients. 250 g of the thus-obtained eluate was mixed with 5 g of Celite 545, followed by suction filtration to obtain 238 g of a filtrate (solid content: 0.74%) which was referred to as a sample of flavor improving agent derived from mango juice.

Polyphenol amounts in terms of chlorogenic acid in each 50 g of the raw fruit juice and the obtained sample were measured and, as a result, the polyphenol amount of the raw fruit juice was found to be 0.361 mmol and that of the sample to be 0.0740 mmol. Then, sugar amounts were measured according to the aforementioned predetermined method. The sugar amount of the raw fruit juice was found to be 99.7 mmol and that of the sample to be 0.0120 mmol. From these results, the raw fruit juice was found to have PP/SG before hydrolysis of 0.00362 and the sample was found to have PP/SG before hydrolysis of 6.17. Also, as a result of measuring the sugar amount in the same manner after acid hydrolysis, the amount of sugar of the raw material was found to be 101 mmol and that of the sample was found to be 0.184 mmol. From these results, the raw fruit juice was found to have PP/SG after hydrolysis of 0.00357 and the sample was found to have PP/SG after hydrolysis of 0.402.

Example 17 and Comparative Example 17

Effect of Giving a Juice-Like Feel

Water was added to 214 g of high fructose corn syrup and 2.6 g of citric acid to prepare 400 g of an aqueous solution and, further, 1,600 g of carbonated water and 2 g of a banana flavor were added thereto to prepare a material. The sample obtained in Example 16 which was derived from mango juice was added to this material to a concentration of 540 ppm to prepare a sample solution of Example 17. Also, for comparison, a sample solution of Comparative Example 17 was prepared by adding the raw mango juice to the material to a concentration of 380 ppm.

For examining difference between the sample solution of Example 17 and the comparative sample solution by sensory evaluation, 10 panelists were asked to compare these by drinking. As a result, with the sample solution to which mango juice was added, 3 out of 10 panelists evaluated as "weak effect of giving a juice-like feel being recognized" and 7 panelists evaluated as "no effects being recognized". On the other hand, with the sample solution of Example 17, 6 out of 10 panelists evaluated as "strong effect of giving a juice-like feel being recognized" and 4 panelists evaluated as "weak effect of giving a juice-like feel being recognized", thus no panelists evaluating the sample solution of Example 17 as "no effects being recognized". Results are shown in Table 9.

TABLE 9

| | Flavor improving agent | Effect of giving a juice-like feel | | |
| --- | --- | --- | --- | --- |
| | | Strong | Weak | No effects |
| Example 17 | Fraction derived from mango juice | 6 | 4 | 0 |
| Comparative Example 17 | Mango juice | 0 | 3 | 7 |

From the above-described results, it has become apparent that the fraction of Example 16 derived from mango juice has the effect of giving a juice-like feel.

Example 18

Preparation of Flavor Improving Agent Derived from Melon Juice 196 g of water was added to 304 g of concentrated melon juice (Bx. 32.8; manufactured by IWATABUSSAN CO., LTD.) to dilute. The water-diluted melon juice obtained had Bx. 20.1. The diluted fruit juice was allowed to pass at a flow rate of SV=5 through a column (column size: inner diameter: 5 cm; height: 9 cm) filled with 120 g of DIAION HP20 (manufactured by Mitsubishi Chemical). After completion of the pass-through operation, 1,060 g of water was allowed to pass through the column at SV=5 for washing. Next, 300 g of a 74% ethanol aqueous solution was allowed to pass through the column at SV=2 to thereby elute adsorbed ingredients. 290 g of the thus-obtained eluate was mixed with 4 g of Celite 545, followed by suction filtration to obtain 276 g of a filtrate (solid content: 0.42%) which was referred to as a sample of flavor improving agent derived from melon juice.

Polyphenol amounts in terms of chlorogenic acid in each 50 g of the raw fruit juice and the obtained sample were measured and, as a result, the polyphenol amount of the raw fruit juice was found to be 0.273 mmol and that of the sample to be 0.0937 mmol. Then, sugar amounts were measured according to the aforementioned predetermined method. The sugar amount of the raw fruit juice was found to be 43.4 mmol, and that of the sample to be 0.0243 mmol. From these results, the raw fruit juice was found to have PP/SG before hydrolysis of 0.00629 and the sample was found to have PP/SG before hydrolysis of 3.86. Also, as a result of measuring the sugar amount in the same manner after acid hydrolysis, the amount of sugar of the raw material was found to be 44.3 mmol and that of the sample was found to be 0.347 mmol. From these results, the raw fruit juice was found to have PP/SG after hydrolysis of 0.00616 and the sample was found to have PP/SG after hydrolysis of 0.270.

Example 19 and Comparative Example 18

Effect of Giving a Juice-Like Feel

Water was added to 214 g of high fructose corn syrup and 2.6 g of citric acid to prepare 400 g of an aqueous solution and, further, 1,600 g of carbonated water and 2 g of an orange flavor were added thereto to prepare a material. The sample obtained in Example 18 which was derived from melon juice was added to this material to a concentration of 950 ppm to prepare a sample solution of Example 19. Further, for comparison, a sample solution of Comparative Example 18 was prepared by adding the raw melon juice to the material to a concentration of 1,070 ppm.

For examining difference between the sample solution of Example 19 and the comparative sample solution by sensory evaluation, 10 panelists were asked to compare these by drinking. As a result, with the sample solution to which melon juice was added, 3 out of 10 panelists evaluated as "weak effect of giving a juice-like feel being recognized" and 7 panelists evaluated as "no effects being recognized". On the other hand, with the sample solution of Example 19, 6 out of 10 panelists evaluated as "strong effect of giving a juice-like feel being recognized" and 4 panelists evaluated as "weak effect of giving a juice-like feel being recognized", thus no panelists evaluating the sample solution of Example 19 as "no effects being recognized". Results are shown in Table 10.

TABLE 10

| | Flavor improving agent | Effect of giving a juice-like feel | | |
|---|---|---|---|---|
| | | Strong | Weak | No effects |
| Example 19 | Fraction derived from melon juice | 6 | 4 | 0 |
| Comparative Example 18 | Melon juice | 0 | 3 | 7 |

From the above-described results, it has become apparent that the fraction of Example 18 derived from melon juice has the effect of giving a juice-like feel.

Example 20

Preparation of Flavor Improving Agent Derived from Orange Juice 350 g of water was added to 300 g of concentrated orange juice (Bx. 40.9; manufactured by CIS SICILY) to dilute. The water-diluted orange juice obtained had Bx. 18.9. The diluted fruit juice was allowed to pass at a flow rate of SV=10 through a column (column size: inner diameter: 3 cm; height: 12.1 cm) filled with 60 g of AMBERLITE XAD-1180 (manufactured by Organo Corporation). After completion of the pass-through operation, 500 g of water was allowed to pass through the column at SV=10 for washing. Next, 140 g of a 92% ethanol aqueous solution was allowed to pass through the column at SV=4 to thereby elute adsorbed ingredients. 140 g of the thus-obtained eluate (solid content: 0.30%) was referred to as a sample of flavor improving agent derived from orange juice.

Polyphenol amounts in terms of chlorogenic acid in each 50 g of the raw fruit juice and the obtained sample were measured and, as a result, the polyphenol amount of the raw fruit juice was found to be 0.310 mmol and that of the sample to be 0.314 mmol. Then, sugar amounts were measured according to the aforementioned predetermined method. The sugar amount of the raw fruit juice was found to be 39.4 mmol and that of the sample to be 0.0357 mmol. From these results, the raw fruit juice was found to have PP/SG before hydrolysis of 0.00787 and the sample was found to have PP/SG before hydrolysis of 8.80. Also, as a result of measuring the sugar amount in the same manner after acid hydrolysis, the amount of sugar of the raw material was found to be 40.1 mmol and that of the sample was found to be 0.693 mmol. From these results, the raw fruit juice was found to have PP/SG after hydrolysis of 0.00773, and the sample was found to have PP/SG after hydrolysis of 0.453.

Example 21 and Comparative Examples 19 and 20

Effect of Suppressing Sourness of Apple Vinegar

Commercially available drinking vinegar "Ringo Su" (apple vinegar) (manufactured by Mizkan Co., Ltd.) was diluted with 5.25-fold amount of water, and the sample obtained in Example 20 which was derived from orange juice was added thereto to a concentration of 10,000 ppm to prepare a sample solution of Example 21. Further, for comparison, there were prepared a sample solution of Comparative Example 19 by adding the raw concentrated orange juice to the diluted Ringo Su to a concentration of 21,500 ppm and a sample solution of Comparative Example 20 by adding a 1% hesperidin mixture solution (hesperidin (manufactured by TCI):αG hesperidin (manufactured by Toyo Sugar Refining Co., Ltd.)=3:7) to the diluted Ringo Su to a concentration of 10,000 ppm.

For examining difference between the sample solution of Example 21 and the comparative sample solution by sensory evaluation, 9 panelists were asked to compare these by drinking. As a result, with the sample solution to which orange juice was added, 3 out of 9 panelists evaluated as "weak sourness-suppressing effect being recognized" and 6 panelists evaluated as "no effects being recognized". With the sample solution to which the hesperidin mixture solution was added, 3 out of 9 panelists evaluated as "weak sourness-suppressing effect being recognized", and 6 evaluated as "no effects being recognized". On the other hand, with the sample solution of Example 21, 8 out of 9 panelists evaluated as "strong sourness-suppressing effect being recognized" and 1 panelist evaluated as "weak sourness-suppressing effect being recognized", thus no panelists evaluating the sample solution of Example 21 as "no effects being recognized". Results are shown in Table 11.

TABLE 11

| | Flavor improving agent | Suppression effect of sourness | | |
|---|---|---|---|---|
| | | Strong | Weak | No effects |
| Example 21 | Fraction derived from orange juice | 8 | 1 | 0 |
| Comparative Example 19 | Orange juice | 0 | 3 | 6 |
| Comparative Example 20 | Hesperidin mixture | 0 | 3 | 6 |

From the above-described results, it has become apparent that the fraction of Example 20 derived from orange juice has the effect of reducing sourness of apple vinegar.

Example 22

Preparation of Flavor Improving Agent Derived from Pear Juice 248 g of water was added to 433 g of concentrated pear juice (Bx. 70.5) to dilute. The water-diluted pear juice obtained had Bx. 45.0. The diluted fruit juice was allowed to pass at a flow rate of SV=1 through a column (column size: inner diameter: 5 cm; height: 23 cm) filled with 300 g of DIAION HP20 (manufactured by Mitsubishi Chemical). After completion of the pass-through operation, 2600 g of water was allowed to pass through the column at SV=5 for washing. Next, 700 g of a 92% ethanol aqueous solution was allowed to pass through the column at SV=3 to thereby elute adsorbed ingredients. 690 g of the thus-obtained eluate was referred to as a sample of flavor improving agent (solid content: 0.18%) derived from pear juice.

Polyphenol amounts in terms of chlorogenic acid in each 50 g of the raw fruit juice and the obtained sample were measured and, as a result, the polyphenol amount of the raw fruit juice was found to be 0.462 mmol and that of the sample to be 0.245 mmol. Then, sugar amounts were measured according to the aforementioned predetermined method. The sugar amount of the raw fruit juice was found to be 162 mmol and that of the sample to be 0.00653 mmol. From these results, the raw fruit juice was found to have PP/SG before hydrolysis of 0.00285 and the sample was found to have PP/SG before hydrolysis of 37.5. Also, as a result of measuring the sugar amount in the same manner after acid hydrolysis, the amount of sugar of the raw material was found to be 162 mmol and that of the sample was found to be 0.107 mmol. From these results, the raw fruit juice was found to have PP/SG after hydrolysis of 0.00285, and the sample was found to have PP/SG after hydrolysis of 2.29.

Example 23 and Comparative Examples 21 and 22

Suppression of Sourness of Citric Acid Aqueous Solution

Citric acid anhydride (manufactured by Junsei Chemical Co., Ltd.) was dissolved in water to prepare a 0.4% aqueous solution thereof. The sample obtained in Example 22 which was derived from pear juice was added thereto to a concentration of 100 ppm to prepare a sample solution of Example 23. Further, for comparison, there were prepared a sample solution of Comparative Example 21 by adding the raw concentrated pear juice to the citric acid aqueous solution to a concentration of 65 ppm and a sample solution of Comparative Example 22 by adding a 1% hesperidin mixture solution (hesperidin (manufactured by TCI):αG hesperidin (manufactured by Toyo Sugar Refining Co., Ltd.)=3:7) to the citric acid aqueous solution to a concentration of 100 ppm.

For examining difference between the sample solutions of Example 23 and the comparative sample solutions by sensory evaluation, 8 panelists were asked to compare these by drinking. As a result, with the sample solution to which pear juice was added, 3 out of 8 panelists evaluated as "weak sourness-suppressing effect being recognized" and 5 panelists evaluated as "no effects being recognized". With the sample solution to which the hesperidin mixture solution was added, 2 out of 8 panelists evaluated as "weak sourness-suppressing effect being recognized", and 6 evaluated as "no effects being recognized". On the other hand, with the sample solution of Example 23, 6 out of 8 panelists evaluated as "strong sourness-suppressing effect being recognized" and 2 panelists evaluated as "weak sourness-suppressing effect being recognized", thus no panelists evaluating the sample solution of Example 23 as "no effects being recognized". Results of these are shown in Table 12.

TABLE 12

| | Flavor improving agent | Suppression effect of sourness | | |
| --- | --- | --- | --- | --- |
| | | Strong | Weak | No effects |
| Example 23 | Fraction derived from pear juice | 6 | 2 | 0 |
| Comparative Example 21 | Pear juice | 0 | 3 | 5 |
| Comparative Example 22 | Hesperidin mixture | 0 | 2 | 6 |

From the above-described results, it has become apparent that the fraction of Example 22 derived from pear juice has the effect of reducing sourness of citric acid.

Example 24

Preparation of Flavor Improving Agent Derived from Banana Juice 350 g of water was added to 213 g of banana concentrated cloudy juice (Bx. 22.7; manufactured by Nankai Kako K.K.) to dilute. This diluted fruit juice was mixed with 25 g of Celite 545, followed by suction filtration to obtain 500 g of a diluted fruit juice (8.6 Bx.) from which fibrous substances were removed. This juice was allowed to pass at a flow rate of SV=4 through a column (column size: inner diameter: 3 cm; height: 10.4 cm) filled with 50 g of DIAION HP20 (manufactured by Mitsubishi Chemical). After completion of the pass-through operation, 440 g of water was allowed to pass through the column at SV=4 for washing. Next, 190 g of a 74% ethanol aqueous solution was allowed to pass through the column at SV=4 to thereby elute adsorbed ingredients. 190 g of the thus-obtained eluate was mixed with 2 g of Celite 545, followed by suction filtration. 175 g of the thus-obtained eluate was referred to as a sample of flavor improving agent (solid content: 0.12%) derived from banana juice.

Polyphenol amounts in terms of chlorogenic acid in each 50 g of the raw fruit juice and the obtained sample were measured and, as a result, the polyphenol amount of the raw fruit juice was found to be 0.274 mmol and that of the sample to be 0.0800 mmol. Then, sugar amounts were measured according to the aforementioned predetermined method. The sugar amount of the raw fruit juice was found to be 34.1 mmol and that of the sample to be 0.00286 mmol. From these results, the raw fruit juice was found to have PP/SG before hydrolysis of 0.00804, and the sample was found to have PP/SG before hydrolysis of 28.0. Also, as a result of measuring the sugar amount in the same manner after acid hydrolysis according to the aforementioned predetermined method, the amount of sugar of the raw material was found to be 34.3 mmol and that of the sample was found to be 0.0486 mmol. From these results, the raw fruit juice was found to have PP/SG after hydrolysis of 0.00799 and the sample was found to have PP/SG after hydrolysis of 1.65.

Example 25 and Comparative Example 23

Effect of Giving a Richness 5.3 g of a dry solid soup "Ajinomoto kk konsome (consommé) (block type)" (manufactured by Ajinomoto Co., Inc.) was dissolved in 300 ml of hot water to prepare a solution. The sample obtained in Example 24 which was derived from banana juice was added to the solution to a concentration of 100 ppm to prepare a sample solution of Example 25. Further, for comparison, a comparative sample solution of Comparative Example 23 was prepared by adding the raw concentrated banana juice to the soup to a concentration of 120 ppm.

For examining difference between the sample solution of Example 25 and the comparative sample solution by sensory evaluation, 9 panelists were asked to compare these by drinking. As a result, with the sample solution to which banana juice was added, 2 out of 9 panelists evaluated as "weak effect of giving a richness being recognized" and 7 panelists evaluated as "no effects being recognized". On the other hand, with the sample solution of Example 25, 9 out of 9 panelists evaluated as "strong effect of giving a richness being recognized", thus no panelists evaluating the sample solution of Example 25 as "no effects being recognized". Results are shown in Table 13.

TABLE 13

| | Flavor improving agent | Effect of giving a richness | | |
| --- | --- | --- | --- | --- |
| | | Strong | Weak | No effects |
| Example 25 | Fraction derived from banana juice | 9 | 0 | 0 |
| Comparative Example 23 | Banana juice | 0 | 2 | 7 |

From the above-described results, it has become apparent that the fraction of Example 24 derived from banana juice has the effect of giving a richness.

Example 26

Preparation of Flavor Improving Agent Derived from Lemon Juice 250 g of concentrated lemon juice (Bx. 43.2; manufactured by CIS SICILY) was allowed to pass at a flow rate of SV=1 through a column (column size: inner diameter: 5 cm; height: 15 cm) filled with 200 g of DIAION HP20 (manufactured by Mitsubishi Chemical). After completion of the pass-through operation, 1,500 g of water was allowed to pass though the column at SV=5 for washing. Next, 500 g of a 74% ethanol aqueous solution was allowed to pass though the column at SV=2 to thereby elute adsorbed ingredients. 500 g of the thus-obtained eluate (solid content: 0.22%) was referred to as a sample of flavor improving agent derived from lemon juice.

Polyphenol amounts in terms of chlorogenic acid in each 50 g of the raw fruit juice and the obtained sample were measured and, as a result, the polyphenol amount of the raw fruit juice was found to be 0.288 mmol and that of the sample to be 0.0956 mmol. Then, sugar amounts were measured according to the aforementioned predetermined method. The sugar amount of the raw fruit juice was found to be 65.4 mmol and that of the sample to be 0.00500 mmol. From these results, the raw fruit juice was found to have PP/SG before hydrolysis of 0.00440 and the sample was found to have PP/SG before hydrolysis of 19.1. Also, as a result of measuring the sugar amount in the same manner after acid hydrolysis, the amount of sugar of the raw fruit juice was found to be 65.8 mmol and that of the sample was found to be 0.109 mmol. From these results, the raw fruit juice was found to have PP/SG after hydrolysis of 0.00438 and the sample was found to have PP/SG after hydrolysis of 0.877.

Example 27 and Comparative Example 24

Effect of Giving a Juice-Like Feel

Water was added to 214 g of high fructose corn syrup and 2.6 g of citric acid to prepare 400 g of an aqueous solution and, further, 1,600 g of carbonated water and 2 g of an apple flavor were added thereto to prepare a material. The sample obtained in Example 26 which was derived from lemon juice was added to this material to a concentration of 1,800 ppm to prepare a sample solution of Example 27. Further, for comparison, a sample solution of Comparative Example 24 was prepared by adding the raw apple juice to the material to a concentration of 900 ppm.

For examining difference between the sample solution of Example 27 and the comparative sample solution by sensory evaluation, 10 panelists were asked to compare these by drinking. As a result, with the sample solution to which lemon juice was added, 3 out of 10 panelists evaluated as "weak effect of giving a juice-like feel being recognized" and 7 panelists evaluated as "no effects being recognized". On the other hand, with the sample solution of Example 27, 8 out of 10 panelists evaluated as "strong effect of giving a juice-like feel being recognized" and 2 panelists evaluated as "weak effect of giving a juice-like feel being recognized", thus no panelists evaluating the sample solution of Example 27 as "no effects being recognized". Results are shown in Table 14.

TABLE 14

| | Flavor improving agent | Effect of giving a juice-like feel | | |
| --- | --- | --- | --- | --- |
| | | Strong | Weak | No effects |
| Example 27 | Fraction derived from lemon juice | 8 | 2 | 0 |
| Comparative Example 24 | Lemon juice | 0 | 3 | 7 |

From the above-described results, it has become apparent that the fraction of Example 26 derived from lemon juice has the effect of giving a juice-like feel.

Example 28

Preparation of Flavor Improving Agent Derived from Lime Juice 250 g of water was added to 180 g of concentrated lime juice (Bx. 44.3; manufactured by CIS SICILY) to dilute. The water-diluted pear juice obtained had Bx. 18.5. The diluted fruit juice was allowed to pass at a flow rate of SV=5 through a column (column size: inner diameter: 5 cm; height: 7.5 cm) filled with 100 g of DIAION HP20 (manufactured by Mitsubishi Chemical). After completion of the pass-through operation, 880 g of water was allowed to pass through the column at SV=5 for washing. Next, 240 g of a 92% ethanol aqueous solution was allowed to pass through the column at SV=2 to thereby elute adsorbed ingredients. 240 g of the thus-obtained eluate (solid content: 0.17%) was referred to as a sample of flavor improving agent derived from lime juice.

Polyphenol amounts in terms of chlorogenic acid in each 50 g of the raw fruit juice and the obtained sample were measured and, as a result, the polyphenol amount of the raw fruit juice was found to be 0.247 mmol and that of the sample to be 0.160 mmol. Then, sugar amounts were measured according to the aforementioned predetermined method, and the sugar amount of the raw fruit juice was found to be 71.1 mmol and that of the sample to be 0.0167 mmol. From these results, the raw fruit juice was found to have PP/SG before hydrolysis of 0.00347 and the sample was found to have PP/SG before hydrolysis of 9.58. Also, as a result of measuring the sugar amount in the same manner after acid hydrolysis, the amount of sugar of the raw fruit juice was found to be 71.2 mmol and that of the sample was found to be 0.133 mmol. From these results, the raw fruit juice was found to have PP/SG after hydrolysis of 0.00347 and the sample was found to have PP/SG after hydrolysis of 1.20.

Example 29 and Comparative Examples 25 and 26

Effect of Suppressing Harsh Taste of Vegetables

The sample obtained in Example 28 which was derived from lime juice was added to commercially available green juice "Super Aojiru" (manufactured by Fancl Corporation) to a concentration of 15,000 ppm to prepare a sample solution of Example 29. Further, for comparison, there were prepared a sample solution of Comparative Example 25 by adding the raw concentrated lime juice to Super Aojiru to a concentration of 11,500 ppm and a sample solution of Comparative Example 26 by adding a 1% hesperidin mixture solution (hesperidin (manufactured by TCI):αG hesperidin (manufactured by Toyo Sugar Refining Co., Ltd.)=3:7) to Super Aojiru to a concentration of 15,000 ppm.

For examining difference between the sample solution of Example 29 and the comparative sample solutions by sensory evaluation, 10 panelists were asked to compare these by drinking. As a result, with the sample solution to which lime juice was added, 3 out of 10 panelists evaluated as "weak harsh taste-suppressing effect being recognized" and 7 panelists evaluated as "no effects being recognized". With the sample solution to which the hesperidin mixture solution was added, 4 out of 10 panelists evaluated as "weak harsh taste-suppressing effect being recognized" and 6 evaluated as "no effects being recognized". On the other hand, with the sample solution of Example 29, 7 out of 10 panelists evaluated as "strong harsh taste-suppressing effect being recognized" and 3 panelists evaluated as "weak harsh taste-suppressing effect being recognized", thus no panelists evaluating the sample solution of Example 29 as "no effects being recognized". Results are shown in Table 15.

TABLE 15

| | Flavor improving agent | Suppression effect of harsh taste | | |
|---|---|---|---|---|
| | | Strong | Weak | No effects |
| Example 29 | Fraction derived from lime juice | 7 | 3 | 0 |
| Comparative Example 25 | Lime juice | 0 | 3 | 7 |
| Comparative Example 26 | Hesperidin mixture | 0 | 4 | 6 |

From the above-described results, it has become apparent that the fraction of Example 28 derived from lime juice has the effect of reducing harsh taste of vegetables.

Example 30

Preparation of Flavor Improving Agent Derived from Grapefruit Juice 250 g of water was added to 200 g of concentrated grapefruit juice (Bx. 54.1; manufactured by CIS SICILY) to dilute. The water-diluted grapefruits juice obtained had Bx. 24.0. The diluted fruit juice was allowed to pass at a flow rate of SV=3 through a column (column size: inner diameter: 5 cm; height: 7.5 cm) filled with 100 g of DIAION HP20 (manufactured by Mitsubishi Chemical). After completion of the pass-through operation, 880 g of water was allowed to pass through the column at SV=5 for washing. Next, 250 g of a 74% ethanol aqueous solution was allowed to pass through the column at SV=2 to thereby elute adsorbed ingredients. 250 g of the thus-obtained eluate (solid content: 0.19%) was referred to as a sample of flavor improving agent derived from grapefruit juice.

Polyphenol amounts in terms of chlorogenic acid in each 50 g of the raw fruit juice and the obtained sample were measured and, as a result, the polyphenol amount of the raw fruit juice was found to be 0.337 mmol and that of the sample to be 0.204 mmol. Then, sugar amounts were measured according to the aforementioned predetermined method. The sugar amount of the raw fruit juice was found to be 61.4 mmol and that of the sample to be 0.0100 mmol. From these results, the raw fruit juice was found to have PP/SG before hydrolysis of 0.00549 and the sample was found to have PP/SG before hydrolysis of 20.4. Also, as a result of measuring the sugar amount in the same manner after acid hydrolysis, the amount of sugar of the raw fruit juice was found to be 61.7 mmol and that of the sample was found to be 0.174 mmol. From these results, the raw fruit juice was found to have PP/SG after hydrolysis of 0.00546 and the sample was found to have PP/SG after hydrolysis of 1.17.

Example 31 and Comparative Examples 27 and 28

Effect of Suppressing Bitterness of Caffeine

Anhydrous caffeine (manufactured by NACALAI TESQUE, INC.) was dissolved in water to prepare a 0.04% caffeine aqueous solution. The sample obtained in Example 30 which was derived from grapefruit juice was added to the aqueous solution to a concentration of 100 ppm to prepare a sample solution of Example 31. Further, for comparison, there were prepared a sample solution of Comparative Example 27 by adding the raw concentrated grapefruit juice to a concentration of 80 ppm and a sample solution of Comparative Example by adding a 1% hesperidin mixture solution (hesperidin (manufactured by TCI):αG hesperidin (manufactured by Toyo Sugar Refining Co., Ltd.)=3:7) to a concentration of 100 ppm.

For examining difference between the sample solution of Example 31 and the comparative sample solutions by sensory evaluation, 7 panelists were asked to compare these by drinking. As a result, with the sample solution to which raw grapefruit juice was added, 3 out of 7 panelists evaluated as "weak bitterness-suppressing effect being recognized" and 4 panelists evaluated as "no effects being recognized". With the sample solution to which the hesperidin mixture solution was added, 3 out of 7 panelists evaluated as "weak bitterness-suppressing effect being recognized" and 4 evaluated as "no effects being recognized". On the other hand, with the sample solution of Example 31, 5 out of 7 panelists evaluated as "strong bitterness-suppressing effect being recognized", and 2 panelists evaluated as "weak bitterness-suppressing effect being recognized", thus no panelists evaluating the sample solution of Example 31 as "no effects being recognized". Results are shown in Table 16.

TABLE 16

| | Flavor improving agent | Suppression effect of bitterness | | |
|---|---|---|---|---|
| | | Strong | Weak | No effects |
| Example 31 | Fraction derived from grapefruit juice | 5 | 2 | 0 |
| Comparative Example 27 | Grapefruit juice | 0 | 3 | 4 |
| Comparative Example 28 | Hesperidin mixture | 0 | 3 | 4 |

From the above-described results, it has become apparent that the fraction of Example 30 derived from grapefruit juice has the effect of reducing bitterness.

The invention claimed is:
1. A method of producing a flavor improving agent, the method comprising:

contacting a fruit juice or squeeze with a synthetic resin absorbant to absorb a fraction of ingredients of the fruit juice or squeeze;

desoring the ingredients on the synthetic resin absorbant with a solvent to produce a flavor improving agent containing the desorbed ingredients, wherein a molar ratio of polyphenols to saccharides of the flavor improving agent after acid hydrolysis is in a range of 0.1 to 10 and a molar ration of polyphenols to saccharides of the flavor improving agent before acid hydrolysis is in a range of 1 to 100.

2. A method of producing a flavor improving agent by extracting a fruit juice or squeeze with a solvent to obtain a flavor improving agent which includes a fraction of ingredients of the fruit juice or squeeze, wherein a molar ratio of polyphenols to saccharides of the flavor improving agent after acid hydrolysis is in a range of 0.1 to 10 and a molar ration of polyphenols to saccharides of the flavor improving agent before acid hydrolysis is in a range of 1 to 100.

3. The method of producing a flavor improving agent according to claim 1, wherein the fruit juice or squeeze is obtained from fruit selected from the group consisting of orange, lemon, grapefruit, lime, blueberry, strawberry, apple, pear, grape, melon, pineapple, peach, mango, and banana.

4. The method of producing a flavor improving agent according to claim 1, wherein the solvent used for eluting the adsorbed ingredients is one selected from the group consisting of water, methanol, ethanol, acetone, ethyl acetate, and a mixture thereof.

5. The method of producing a flavor improving agent according to claim 2, wherein the fruit juice or squeeze is obtained from fruit selected from the group consisting of orange, lemon, grapefruit, lime, blueberry, strawberry, apple, pear, grape, melon, pineapple, peach, mango, and banana.

6. The method of producing a flavor improving agent according to claim 2, wherein the solvent is one selected from the group consisting of water, methanol, ethanol, acetone, ethyl acetate, and a mixture thereof.

7. A method of improving the flavor of a composition, the method comprising combining the flavor improving agent of claim 1 with a food, beverage, pharmaceutical product, or oral care product to form the composition.

* * * * *